United States Patent
Leysen et al.

(12)

(10) Patent No.: US 6,528,501 B1
(45) Date of Patent: Mar. 4, 2003

(54) 22S-HYDROXYCHOLESTA-8, 14-DIENE DERIVATIVES WITH MEIOSIS REGULATING ACTIVITY

(75) Inventors: Dirk D. Leysen, Lommel (BE); Jaap J. van der Louw, En Oss (NL); Robert Gerard Jules Marie Hanssen, Heesch (NL); A. Anja Wiersma, He Elst (NL)

(73) Assignee: Akzo Nobel N.V., Arnhem (NL)

(*) Notice: Subject to any disclaimer, the term of this patent is extended or adjusted under 35 U.S.C. 154(b) by 0 days.

(21) Appl. No.: 09/857,731

(22) PCT Filed: Jun. 10, 1999

(86) PCT No.: PCT/EP99/04099

§ 371 (c)(1),
(2), (4) Date: Jul. 16, 2001

(87) PCT Pub. No.: WO00/35938

PCT Pub. Date: Jun. 22, 2000

(30) Foreign Application Priority Data

Dec. 11, 1998 (EP) .............................................. 98/08130

(51) Int. Cl.$^7$ ........................... C07J 9/00; A61K 31/578
(52) U.S. Cl. ...................... 514/177; 514/182; 552/548; 552/552; 552/556
(58) Field of Search ................................ 552/548, 552, 552/556; 514/182

(56) References Cited

U.S. PATENT DOCUMENTS 5,716,777 A * 2/1998 Byskov et al. ................. 435/2

FOREIGN PATENT DOCUMENTS

| WO | WO 96 00235 A | | 1/1996 |
|---|---|---|---|
| WO | 9600235 | * | 1/1996 |
| WO | WO 96 27658 A | | 9/1996 |
| WO | WO 97 00884 A | | 1/1997 |
| WO | WO 98 28323 A | | 7/1998 |
| WO | WO 99 32506 A | | 7/1999 |

OTHER PUBLICATIONS

Byskov. A. G. et al.: "Chemical Structure of Sterols That Activate Oocyte Meiosis", Nature, vol. 374, No. 6522, Apr. 6, 1995, pp. 559–562.

Yuzo Yoshida et al.: "Sterol 14–Demethylase P450 Activity Expressed in Rat Gonads: Contribution to the Formation of Mammalian Meiosis–Activating Sterol", Biochemical and Biophysical Research Communications, vol. 223, No. 3, Jun. 25, 1996, pp. 534–538.

C. Grondahl et al.: "Meiosis Activating Sterol Promotes Resumption of Meiosis in Mouse Oocytes Cultured In Vitro in Contrast to Related Oxysterols", p. 417, col. 1. Chemical Abstracts, vol. 129, No. 4, Jul. 27, 1998, abstract No. 39307.

C. Grondahl et al.: Biological Reproduction, vol. 58, No. 5, 1998, pp. 1297–1302.

R.J. Chorvat et al.: "22–Hydroxycholesterol Derivatives as HMG CoA Reductase Suppressors and Serum Cholesterol Lowering Agents", Journal Of Medicinal Chemistry, vol. 28, No. 2, Feb. 1985, pp. 194–200.

* cited by examiner

Primary Examiner—Sabiha Qazi
(74) Attorney, Agent, or Firm—Mark W. Milstead; William M Blackstone

(57) ABSTRACT

The invention relates to 22S hydroxycholesta-8, 14-diene derivatives having general formula (I) wherein $R_1$ is OR, $OSO_3H$ or —NOR; with R being H, $(C_{1-6})$alkyl or $(C_{1-6})$ acyl; each of $R_2$ and $R_3$ is independently hydrogen or $(C_{1-6})$alkyl; $R_4$ is hydrogen, $(C_{1-6})$alkyl or $(C_{1-6})$acyl; $R_5$ is hydrogen; or $R_5$ designates, together with $R_6$, an additional bond between the carbon atoms at which $R_5$ and $R_6$ are placed; $R_6$ is hydrogen, hydroxy or halogen, or $R_6$ designates, together with $R_5$, an additional bond between the carbon atoms at which $R_6$ and $R_5$ are placed; each or $R_7$ and $R_8$ is independently hydrogen or $(C_{1-4})$alkyl, optionally substituted with OH, $(C_{1-4})$alkoxy, or halogen; or a pharmaceutically acceptable salt thereof. The compounds of the invention have meiosis activating activity and can be used for the control of fertility.

11 Claims, No Drawings

22S-HYDROXYCHOLESTA-8, 14-DIENE DERIVATIVES WITH MEIOSIS REGULATING ACTIVITY

This application is the 35 U.S.C. §371 filing of PCT/EP99/04099 filed Jun. 10, 1999.

FIELD OF THE INVENTION

The invention relates to 22S-hydroxycholesta-8,14-diene derivatives, to pharmaceutical compositions containing the same, as well as to the use of these 22S-hydroxycholesta-8,14-diene derivatives for the preparation of a medicament for the control of fertility.

BACKGROUND OF THE INVENTION

Sexual reproduction involves a cyclic alternation of diploid and haploid states: diploid cells divide by the process of meiosis to form haploid cells, and the haploid cells fuse in pairs at fertilization to form new diploid cells. The process of meiosis is characterized by two meiotic divisions, unique to both male and female germ cells. During the process two cell divisions, following one round of DNA replication, give rise to four haploid cells from one single diploid cell. Chromosomal crossover events, during which paternal and maternal genetic material is exchanged, occur during the prophase of the first meiotic division. At the end of the first meiotic division one member of each chromosome pair, composed of two sister chromatids is distributed to each daughter cell. The second meiotic division segregates each sister chromatide into a separate haploid cell. Male and female germ cells are subject to similar meiotic divisions but differ in the regulation of these processes. In the male meiosis is a continuous process in germ cells derived from a population of immature germ cells, the stem cell spermatogonia. After sexual maturation of the male, spermatogonia from this stem cell population embark on meiosis. The first and second meiotic division proceed without interruption and eventually give rise to four mature spermatozoa.

In the female, primary oocytes start the first meiotic division already during the embryonic stage but they remain arrested in the prophase (dictyate stage) until the female becomes sexually mature. Meiosis resumes at the time of ovulation (egg maturation) after which the first meiotic division is completed and the second meiotic division is initiated. In most vertebrates the second meiotic division is arrested at the metaphase and only completed after fertilization. At the end of the first and of the second meiotic division the cytoplasm divides asymmetrically to produce two secondary oocytes, each with a haploid number of single chromosomes, but greatly differing in size: one is a small polar body, which eventually degenerates, and the other is a large cell containing all the developmental potential. Finally one mature ovum is produced.

The stage at which the developing oocyte is released from the ovary and is ready for fertilization differs in different species. In both invertebrates and vertebrates ovarian accessory cells respond to polypeptides (gonadotropins) produced elsewhere in the body so as to control the maturation of the oocyte and eventually (in most species) ovulation. In humans the primary oocytes of the newborn female are arrested in prophase of meiotic division I and most are surrounded by a single layer of follicle cells; such an oocyte with its surrounding cells constitute the primordial follicle. A small portion of primordial follicles sequentially begins to grow to become developing follicles: the follicle cells enlarge and proliferate to form a multilayered envelope around the primary oocyte; the oocyte itself enlarges and develops the zona pellucida, an extracellular matrix consisting largely of glycoproteins, and cortical granules, specialized secretory vesicles just under the plasma membrane in the outer region, the cortex, of the egg cytoplasm [when the egg is activated by a sperm, these cortical granules release their contents by exocytosis; the contents of the granules act to alter the egg coat so as to prevent other sperms from fusing with the egg].

The developing follicles grow continuously and some of them develop a fluid-filled cavity, or antrum, to become antral follicles. Development of such follicles is dependent on gonadotropins (mainly follicle stimulating hormone -FSH) secreted by the pituitary gland and on estrogens secreted by the follicle cells themselves. Starting at puberty, a surge of secretion by the pituitary of another gonadotropin, luteinizing hormone (LH), activates a single antral follicle to complete its development: the enclosed primary oocyte matures to complete the meiotic division I as the stimulated follicle rapidly enlarges and ruptures at the surface of the ovary, releasing the secondary oocyte within. As is the case with most mammals, the secondary oocyte is triggered to undergo division II of meiosis only if it is fertilized by a sperm.

Studies on the mechanisms controlling initiation and regulation of the meiotic process in male and female germ cells suggest a role for cyclic nucleotides in mediating meiotic arrest. Spontaneous maturation of oocytes can be prevented by compounds that maintain elevated cAMP levels [Eppig, J. and Downs, S. (1984) Biol. Reprod. 30: 1–11]. Purines, like adenosine or hypoxanthine, are thought to be involved in the cAMP mediated maintenance of meiotic arrest [Eppig, J., Ward-Bailey, P. and Coleman, D. (1985)Biol. Reprod. 33: 1041–1049]. The presence of a meiosis regulating substance in a culture system of fetal mouse gonads was first described by Byskov, A. et al (1976)Dev. Biol. 52: 193–200. It was suggested that the concentrations of a meiosis activating substance (MAS) and a meiosis preventing substance (MPS) regulate the meiotic process in concert [Byskov, A. et al. (1994). In "*The physiology of reproduction*", Eds. Knobil, E. and Neill, J., Raven Press, New York]. More recently (3β,5α,20R)-4,4-dimethylcholesta-8,14,24-trien-3-ol (FF-MAS), isolated from human follicular fluid, and (3β,5α,20R)-4,4-dimethylcholesta-8,24-dien-3-ol, isolated from bull testes, were identified by Byskov, A. et al [(1995), *Nature* 374: 559–562] as endogenous meiosis activating substances in human and bovine, respectively. These sterols proved to be able to activate the resumption of meiosis in cultured cumulus enclosed and naked mouse oocytes.

Derivatives of the endogenous sterols, having either a saturated or an unsaturated cholestane side chain, have been disclosed in the international patent applications WO 96/00235, WO97/00884 and WO98/28323 (NOVO NORDISK A/S) as meiosis regulating substances. Meiosis regulating substances are compounds that are agonists or antagonists of a naturally occurring meiosis activating substance. Thus, they might be used in the treatment of infertility or for contraception.

A drawback of the compounds described in the first two patent applications mentioned above is their restricted membrane penetration, which results in accumulation in cell membranes or fatty tissues, thereby restricting their therapeutic potential as fertility control agents. This unwanted accumulation is most probably due to the fysico-chemical properties of these compounds, which resemble those of cholesterol, an important constituent of cell membranes [Norum, K. R. et al (1983) *Physiological Rev.* 63: 1343; Babiker, A. et al (1998) *Biochimica & Biophysica Acta* 1392: 333].

BRIEF SUMMARY OF THE INVENTION

We have now found, that certain 22S-hydroxy substituted cholestane derivatives, i.e. the 22S-hydroxycholesta-8,14-diene derivatives of formula I given below, are highly active as meiosis activating compounds.

Formula I

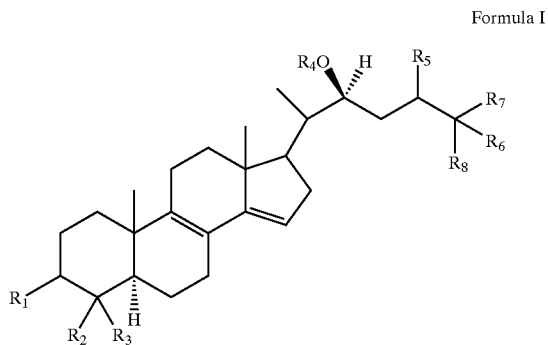

DETAILED DESCRIPTION OF THE INVENTION wherein $R_1$ is OR, $OSO_3H$ or =NOR; with R being H, $(C_{1-6})$alkyl or $(C_{1-6})$acyl;

each of $R_2$ and $R_3$ is independently hydrogen or $(C_{1-6})$ alkyl;

$R_4$ is hydrogen, $(C_{1-6})$alkyl or $(C_{1-6})$acyl;

$R_5$ is hydrogen; or $R_5$ designates, together with $R_6$, an additional bond between the carbon atoms at which $R_5$ and $R_6$ are placed;

$R_6$ is hydrogen, hydroxy or halogen; or $R_6$ designates, together with $R_5$, an additional bond between the carbon atoms at which $R_6$ and $R_5$ are placed;

each of $R_7$ and $R_8$ is independently hydrogen or $(C_{1-4})$ alkyl, optionally substituted with OH, $(C_{1-4})$alkoxy, or halogen;

or a pharmaceutically acceptable salt thereof.

An advantage of 22-hydroxycholestanes is their ability to pass cell membranes which would circumvent the problems described above, see Stocco, D. M. (1997), *Endocrine* 6: 99–109.

The above 22S-hydroxycholesta-8,14-diene derivatives having the general formula I are highly active as meiosis activating substances. In fact, they are active in the CEO assay (see below) wherein even the natural meiosis activating substance FF-Mas is not. This does not follow at all from the prior art. In this respect it is noted that, incidentally, a certain 22R-hydroxy substituted cholestane derivative (22R-hydroxycholesterol) has been disclosed in WO 98/28323, but is an antagonist.

The invention further provides a pharmaceutical composition comprising a 22S-hydroxycholesta-8,14-diene derivative having the general formula I. A further aspect of the invention resides in the use of a 22S-hydroxycholesta-8,14-diene derivative having the general formula I for the manufacture of a medicament for the control of fertility.

The term $(C_{1-6})$alkyl as used in the definition of formula I means a branched or unbranched alkyl group having 1–6 carbon atoms, like hexyl, pentyl, butyl, isobutyl, tertiary butyl, propyl, isopropyl, ethyl and methyl. Likewise, the term $(C_{1-4})$alkyl means an alkyl group having 1–4 carbon atoms.

The term $(C_{1-6})$acyl means an acyl group derived from a carboxylic acid having from 1–6 carbon atoms, like hexanoyl, pentanoyl, pivaloyl, butyryl, propanoyl, acetyl and formyl. Also included within the definition of $(C_{1-6})$acyl are acyl groups derived from dicarboxylic acids, like hemiglutaroyl, hemi-succinoyl, and hemi-maloyl. A preferred $(C_{1-4})$acyl group is hemi-succinoyl.

The term $(C_{1-4})$alkoxy means an alkyloxy having 1–4 carbon atoms, like butyloxy, propyloxy, isopropyloxy, ethyloxy, and, preferably, methyloxy.

The term halogen means F, Cl, Br or I. Cl and F are preferred, F being most preferred.

It is understood that the 22S-hydroxycholesta-8,14-diene derivatives of the invention have the natural configurations 5α, 10β, 13β, and 17β. The configuration at position 20 of the 22S-hydroxycholesta-8,14-diene derivatives of the invention can be either R or S. Preferred compounds are those with the 20S configuration.

Even more preferred compounds according to the invention are the 22S-hydroxycholesta-8,14-diene derivatives of formula I wherein $R_1$ is OR wherein R has the previously given meaning. Among these preferred compounds those with the 3-OR substituent in the β-configuration are especially preferred. A specifically preferred agonistic compound of the invention is the 22S-hydroxycholesta-8,14-diene derivative (3β,5α,20S,22S)-4,4-dimethylcholesta-8,14,24-triene-3,22-diol.

The 22S-hydroxycholesta-8,14-diene derivatives of this invention have the natural configurations 5α, 10β, 13β, 17β, and possess also one or more additional chiral carbon atoms. The compounds may therefore be obtained as a pure diastereomer, or as a mixture of diastereomers. Methods for obtaining the pure diastereomers are well known in the art, e.g. crystallization or chromatography.

The meiosis activating activity of the 22S-hydroxycholesta-8,14-diene derivatives of the invention is measured in an in vitro oocyte assay as the ability to overcome the hypoxanthine maintained meiotic arrest in denuded oocytes (DO) or cumulus enclosed oocytes (CEO).

The compounds can be used to stimulate meiosis in both male and female and thus can be used as fertility regulating agents. Fertility regulation comprises contraception and infertility treatment.

For female contraception a 22S-hydroxycholesta-8,14-diene derivative according to formula I can be used for induction of premature maturation of oocytes which are still inside the ovary, before the naturally occurring gonadotropin surge [reduced fertility by inducing premature maturation of oocytes has been demonstrated in rats by Mattheij, J. et al (1993), *Gynecolo Obstet. Invest.* 36: 129–135]. On in vivo administration the compounds of the invention specifically affect germ cells and therefore have the advantage of maintenance of endogenous hormonal levels and subsequently maintenance of normal cycle length. Such a contraceptive method will not cause unwanted side-effects sometimes associated with steroidal contraception (e.g. thrombosis, mood, unscheduled bleeding, malignant breast disease).

A further advantage of the 22S-hydroxycholesta-8,14-diene derivatives of the invention is their inability to induce maturation in incompetent oocytes (isolated from pre-antral follicles), which indicates that the compounds will not affect the entire oocyte reserve in the ovaries. Only oocytes from antral follicles (competent oocytes) can be induced to mature by the compounds of the invention.

For treatment of female infertility caused by the absence of mature oocytes the compounds of the invention can be administered in vivo to timely stimulate the maturation of competent oocytes.

The compounds of the invention can also be used for suppletion of culture media for in vitro fertilization procedures in order to improve oocyte quality.

For treatment of male infertility caused by a shortage of the number of mature spermatozoa the compounds of the invention can be administered in vivo to stimulate the maturation of spermatogonia.

For therapeutic use, salts of the compounds of formula I are those wherein the counterion is pharmaceutically acceptable. However, salts of the acids according to formula I [i.e. compounds wherein $R_1$ is $OSO_3H$] may also find use, for example, in the preparation or purification of a pharmaceutically acceptable compound. All salts, whether pharmaceutically acceptable or not, are included within the ambit of the present invention. Examples of salts of acids according to the invention are mineral salts such as sodium salt, potassium salt, and salts derived from organic bases like ammonia, imidazole, ethylenediamine, triethylamine and the like.

The compounds of formula I or a pharmaceutically acceptable salt thereof, also referred to herein as the active ingredient, may be administered enterally or parenterally. The exact dose and regimen of administration of the active ingredient, or a pharmaceutical composition thereof, will necessarily be dependent upon the therapeutic effect to be achieved (contraception or infertility), and will vary with the particular compound, the route of administration, and the age and condition of the individual subject to whom the medicament is to be administered.

In general parenteral administration requires lower dosages than other methods of administration which are more dependent upon adsorption. However, a dosage for humans preferably contains 0.0001–25 mg per kg body weight. The desired dose may be presented as one dose or as multiple subdoses administered at appropriate intervals throughout the day, or, in case of female recipients, as doses to be administered at appropriate daily intervals throughout the menstrual cycle. The dosage as well as the regimen of administration may differ between a female and a male recipient.

In case of in vitro or ex vivo applications, the compounds of the inventions are to be used in the incubation media in a concentration of approximately 0.01–5 µg/ml.

The present invention thus also relates to pharmaceutical compositions comprising a 22S-hydroxycholesta-8,14-diene derivative according to formula I in admixture with pharmaceutically acceptable auxiliaries, and optionally other therapeutic agents. The auxilliaries must be "acceptable" in the sense of being compatible with the other ingredients of the composition and not deleterious to the recipients thereof.

Pharmaceutical compositions include those suitable for oral, rectal, nasal, topical (including transdermal, buccal and sublingual), vaginal or parenteral (including subcutaneous, intramuscular, intravenous and intradermal) administration. The compositions may be prepared by any method well known in the art of pharmacy, for example, using methods such as those described in Gennaro et al., Remington's Pharmaceutical Sciences (18th ed., Mack Publishing Company, 1990, see especially Part 8: Pharmaceutical Preparations and Their Manufacture). Such methods include the step of bringing in association the active ingredient with any auxilliary agent. The auxilliary agent(s), also named accessory ingredients, include those conventional in the art (Gennaro, supra), such as, fillers, binders, diluents, disintegrants, lubricants, colorants, flavoring agents and wetting agents.

Pharmaceutical compositions suitable for oral administration may be presented as discrete dosage units such as pills, tablets or capsules, or as a powder or granules, or as a solution or suspension. The active ingredient may also be presented as a bolus or paste. The compositions can further be processed into a suppository or enema for rectal administration.

For parenteral administration, suitable compositions include aqueous and non-aqueous sterile injection. The compositions may be presented in unit-dose or multi-dose containers, for example sealed vials and ampoules, and may be stored in a freeze-dried (lyophilised) condition requiring only the addition of sterile liquid carrier, for example, water prior to use.

Compositions, or formulations, suitable for administration by nasal inhalation include fine dusts or mists which may be generated by means of metered dose pressurised aerosols, nebulisers or insufflators.

The 22S-hydroxycholesta-8,14-diene derivatives of the invention can also be administered in the form of implantable pharmaceutical devices, consisting of a core of active material, encased by a release rate-regulating membrane. Such implants are to be applied subcutaneously or locally, and will release the active ingredient at an approximately constant rate over relatively large periods of time, for instance from weeks to years. Methods for the preparation of implantable pharmaceutical devices as such are known in the art, for example as described in European Patent 0,303,306.

The compounds of the invention may be produced by various methods known in the art of organic chemistry in general, and especially in the art of the chemistry of steroids (see, for example: Fried, J. and Edwards, J. A., "*Organic Reactions in Steroid Chemistry*", Volumes I and II , Van Nostrand Reinhold Company, New York, 1972). A convenient starting material for the preparation of compounds of formula I is a compound of general formula II ,

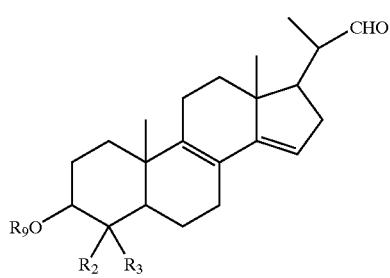

Formula II wherein $R_2$ and $R_3$ are independently hydrogen or ($C_{1-6}$) alkyl, $R_9$ is a hydroxy-protecting group such as an acyl group, like an acetyl group, a benzoyl group or a pivaloyl group, or an alkoxyalkyl group, like an ethoxyethyl group or a tetrahydropyranyl (THP) group, whose preparation is described in WO-09852965 and WO-09855498. Suitable protective groups are known in the art [for example from Greene, T. W. and Wuts, P. G. M.: *Protective Groups in Organic Synthesis,* Second Edition, Wiley, N.Y., 1991.

Starting from this key intermediate, the side-chain is constructed, using methods known in the art [see: Redpath, J. et al, Chem. Soc. Rev. 12, 75 (1983); Zhu, G.-D. et al, Chem. Rev. 95, 1877 (1995); Apfel, M. A., J. Org. Chem. 44, 643 (1979); Kircher, H. W. et al, J. Org. Chem. 52, 2586

(1987); Takeshita, T. et al, Chem. Pharm. Bull. 24, 1928 (1976); Dasgupta, S. K. et al, J. Org. Chem. 39, 1658 (1974); Dolle, R. E. et al, J. Am. Chem. Soc. 111, 278 (1989); Poyser, J. P. et al, J. Chem. Soc., Perkin Trans. I, 2061 (1974)].

For instance, compounds of formula I ($R_1$=OH, $R_4$=H, $R_5$=H) can be prepared by reaction of compounds of formula II with a suitably substituted alkylmetallic reagent of formula III,

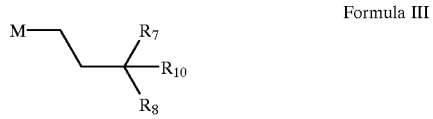

Formula III wherein M is Li, MgX, ZnX, or CeX (X=Cl,Br,I), $R_7$ and $R_8$ have the previously given meaning, any hydroxy group present in $R_7$ or $R_8$ being suitably protected, and $R_{10}$ is H, protected OH, or halogen, which often results in the predominant formation of the 22S-hydroxycholestane derivative [see e.g. Poyser, J. P. et al, J. Chem. Soc., Perkin Trans. I, 2061 (1974)]. The 22S-hydroxy- and 22R-hydroxy derivatives can be separated or, if necessary, the 22R-hydroxy isomer is epimerized to the 22S-hydroxy compound. Epimerization at C-22 can be accomplished e.g. by means of a Mitsunobu reaction [see Hughes, D. L., Organic Reactions 42, 335 (1992)], or by treatment with methanesulfonyl chloride or p-toluenesulfonyl chloride followed by reaction with an oxygen nucleophile [e.g. potassium superoxide, see Corey, E. J. et al, Tetrahedron Lett. 3183 (1975) and Larock, R. C., "Comprehensive Organic Transformations", VCH Publishers, Inc.,1989, p. 479]. In both cases, removal of any remaining protective groups then results in compounds of formula I ($R_1$=OH; $R_4$,$R_5$=H).

Compounds of formula I ($R_1$=OH, $R_4$=H, $R_5$ and $R_6$ together form an additional bond, i.e. a $\Delta^{24}$ double bond) can be obtained from aldehyde II as follows: the latter is reacted with the anion of acetonitrile [$MCH_2C\equiv N$, M=Li, Na, K, MgX, ZnX; see: Arseniyadis, S. et al, Org. React. 31, 1 (1984)] to give a diastereomeric pair of 22R and 22S-hydroxycholane-24-nitrile derivatives. After isolation of the 22S-hydroxy epimer the 22-hydroxy group is protected as a silyl ether or as an alkoxyalkyl ether. If necessary, the 3-hydroxy group is reprotected in the same way, or with an orthogonal protective group. The cyano group is reduced to the corresponding carboxaldehyde group by treatment with a reducing agent such as diisobutylaluminium hydride or other reducing agents capable of converting a carbonitrile group into a carboxaldehyde group. Wittig reaction with a suitably substituted Wittig reagent and removal of protective groups then results in the cholest-24-enes of formula I ($R_1$=OH, $R_4$=H, $R_5$ and $R_6$ together form a $\Delta^{24}$ double bond).

For methods used for the Wittig olefination reaction, see Maercker, A., Org. React. 14, 270 (1965). Alternatively, Peterson reactions can be used, see Ager, D. J. Org. React. 38, 1 (1990).

The Wittig reaction can also be performed in the opposite direction. In that case, the cholan-24-al derivative mentioned above is reduced to the corresponding cholan-24-ol derivative with the use of reducing agents like for example lithium aluminium hydride, sodium borohydride, or other hydride reducing agents known in the art. The 24-hydroxy group is converted to a leaving group, e.g. Br, I, mesyloxy, or tosyloxy. Reaction with an appropriate phosphine (e.g. triphenyl phosphine), Wittig reaction with a suitably substituted ketone, and finally, removal of protective groups then results in the formation of compounds of formula I ($R_1$=OH, $R_4$=H, $R_5$ and $R_6$ together form a $\Delta^{24}$ double bond).

Construction of $\Delta^{24}$-cholestanes I from aldehydes II can also be accomplished by an analogous reaction sequence which makes use of anions of acetic acid or anions of acetic acid esters [see: Petragnani, N. et al, Synthesis, 521 (1982)]. Techniques for homologation are known in the art, see for example Mathieu, J. et al: Formation of C—C Bonds, Vol. I–III, Georg Thieme Publishers, Stuttgart, 1973.

Selective deprotection of 3-OH and 22-OH enables independent conversion, using methods known in the art, of 3-OH into 3-OR, $OSO_3H$ or =NOR (R as previously defined), and of 22-OH into 22-$OR_4$ ($R_4$ as previously defined), respectively.

The invention is further illustrated by the following examples.

EXAMPLE 1

(3β,5α,20S ,22S)-4,4-Dimethylcholesta-8,14-diene-3,22-diol i)—A solution of 3-methylbutylmagnesium iodide (12 ml), prepared from 1-iodo-3-methylbutane (2.36 ml) and magnesium (0.48 g), activated with 1,2-dibromoethane (0.040 ml), in diethyl ether (10 ml and 10 ml, respectively) at reflux temperature, was added dropwise to (3β,5α,20S)-3-(benzoyloxy)-4,4-dimethylpregna-8,14-diene-20-carboxaldehyde (WO-09852965; 1.55 g) in THF (20 ml). The reaction mixture was stirred at room temperature for 45 min. and then poured into a saturated aqueous solution of ammonium chloride. The product was extracted into ethyl acetate; the combined organic phases were washed with a saturated aqueous solution of ammonium chloride and with brine, dried over magnesium sulfate and concentrated under reduced pressure. Column chromatography afforded (3β,5α,20S,22S)-4,4-dimethylcholesta-8,14-diene-3,22-diol 3-benzoate (1.1 g).

ii)—A solution of the product obtained under i (0.35 g) in dry tetrahydrofuran (5 ml) was added dropwise to an ice-cooled suspension of lithium aluminium hydride (0.075 g) in dry tetrahydrofuran (5 ml). The mixture was stirred at room temperature for 30 min. The reaction mixture was cooled to 0° C., and then quenched with a saturated aqueous solution of sodium sulfate. Then it was filtered over dicalite and the filtrate concentrated under reduced pressure to give, after column chromatography, (3β,5α,20S,22S)-4,4-dimethylcholesta-8,14-diene-3,22-diol (0.18 g), m.p. 142–143° C.

EXAMPLE 2

(3β,5α,20S,22S)-4,4-Dimethylcholesta-8,14,24-triene-3,22-diol i)—Tetrapropylammonium perruthenate (0.180 g) was added to a solution of (3β,5α,20S)-4,4,20-trimethylpregna-8,14-diene-3,21-diol 3-benzoate (WO09852965; 4.62 g) and 4-methylmorpholine N-oxide (3.50 g) in acetone (80 ml). After 30 min. stirring at room temperature the reaction mixture was filtered over dicalite and silica. The filtrate was concentrated under reduced pressure, to give (3β,5α,20S)-3-(benzoyloxy)-4,4-dimethylpregna-8,14-diene-20-carboxaldehyde (4.28 g) which was used in the following step without further purification.

ii)—A solution of diisopropylamine (8.40 ml) in dry THF (100 ml) was cooled to −30° C. n-BuLi (1.6 M solution in hexanes, 37.6 ml) was added dropwise while the temperature was allowed to raise to −5° C. Stirring was continued for 10 min. whereafter the reaction mixture was cooled to −78° C. Acetonitrile (3.14 ml) was added dropwise in 5 min. and stirring was continued for another 30 min. A solution of the aldehyde obtained in the previous step (4.28 g) in THF (60 ml) was added dropwise and the mixture was stirred at −78° C. for 2 h. Then it was poured into a saturated aqueous solution of ammonium chloride and the product was extracted into ethyl acetate. The combined organic phases were washed with brine, dried over sodium sulfate and concentrated under reduced pressure. Column chromatography afforded (3β,5α,20S,22R)-3,22-dihydroxy-4,4-dimethylchola-8,14-diene-24-nitrile (1.23 g) and (3β,5α,20S,22S)-3,22-dihydroxy-4,4-dimethylchola-8,14-diene-24-nitrile (0.85 g).

iii)—Pyridinium p-toluenesulfonate (0.20 g) was added to a solution of (3β,5α,20S,22S)-3,22-dihydroxy-4,4-dimethylchola-8,14-diene-24-nitrile (0.70 g), in dichloromethane (8 ml) and ethyl vinyl ether (4 ml). After stirring of the reaction mixture for 1 h at room temperature the mixture was poured into a saturated aqueous solution of sodium hydrogencarbonate. The product was extracted into diethyl ether; the combined organic phases were washed with brine, dried over sodium sulfate, and concentrated under reduced pressure to give (3β,5α,20S,22S)-3,22-bis[(1-ethoxyethyl)oxy]-4,4-dimethylchola-8,14-diene-24-nitrile (1.0 g), which was used in the following step without further purification.

iv)—Diisobutylaluminium hydride (20% solution in toluene, 8 ml) was cooled to −78° C. A solution of the compound obtained in the previous step (1.0 g) in dry THF (10 ml) was added dropwise and stirring was continued for 15 min. at −78° C. and then for 1.5 h at 0° C. The reaction was quenched with an aqueous solution of acetic acid (20%, 0° C.). The reaction mixture was poured into a saturated aqueous solution of sodium hydrogencarbonate and the product was extracted into diethyl ether. The combined organic phases were washed with brine, dried over sodium sulfate, and concentrated under reduced pressure to give (3β,5α,20S,22S)-3,22-bis[(1-ethoxyethyl)oxy]-4,4-dimethylchola-8,14-dien-24-al (0.96 g), which was used in the following step without further purification.

v)—A suspension of i-propyltriphenylphosphonium iodide (4.57 g) in dry THF (20 ml) was cooled to −30° C. n-BuLi (1.6 M solution in hexanes, 6.50 ml) was added dropwise whereafter the temperature was allowed to raise to 0° C. in 30 min. Stirring was continued for 30 min. at 0° C. and then for another 30 min. at room temperature. After cooling to −30° C., a solution of the aldehyde obtained in the previous step (0.96 g) in THF (15 ml) was added and the mixture was stirred for 1 h while the temperature was allowed to raise to room temperature. Then it was poured into a saturated aqueous solution of ammonium chloride and the product was extracted into diethyl ether. The combined organic phases were washed with brine, dried over sodium sulfate and concentrated under reduced pressure, to give a mixture of (3β,5α,20S,22S)-3,22-bis[(1-ethoxyethyl)oxy]-4,4-dimethylcholesta-8,14,24-triene, phosphonium salt and triphenylphosphine oxide (1.86 g), which was used in the following step without further purification.

vi)—A mixture of silica (12 g), a saturated aqueous solution of oxalic acid (2 ml), and dichloromethane (20 ml) was stirred at room temperature for 10 min. A solution of the product obtained in the previous step (1.86 g) in dichloromethane (10 ml) was added and stirring was continued for 3 h. The reaction mixture was filtered and the filtrate was concentrated under reduced pressure. Column chromatography of the crude product afforded (3β,5α,20S,22S)-4,4-dimethylcholesta-8,14,24-triene-3,22-diol (0.25 g), m.p. 106–108° C.

EXAMPLE 3

The Oocyte Assay

General:

Oocytes arrested in meiosis contain diffused chromosomes which are surrounded by an intact nuclear envelope known as the germinal vesicle (GV). Upon reinitiation of meiosis by the midcycle gonadotropin surge, the chromosomes recondense and the GV breaks down (GVBD). In vivo, the oocyte is exposed to hypoxanthine (HX), which maintains the oocyte arrested in the meiotic prophase. This meiotic arrest can be mimicked in vitro by addition of hypoxanthine to the culture medium. The agonistic activity of the meiosis activating substances is measured as the ability to overcome the hypoxanthine maintained meiotic arrest in denuded oocytes (DO) or cumulus enclosed oocytes (CEO), i.e. as the ability to induce meiotic resumption in vitro.

Isolation of Cumulus Enclosed Oocytes:

Ovaries are obtained from immature female mice (B6D2-F1, strain C57BL×DBA). At the age of 19, 20 or 21 days the mice are injected subcutaneously with a single dose of 20 IU follicle stimulating hormone (Humegon, Organon, The Netherlands) in saline.

Forty-eight hours after follicle stimulating hormone injection mice are killed by cervical dislocation. The ovaries are removed, freed of extraneous tissue and placed in a multi-dish containing 0.5 ml preparation medium at 37° C. L-15 Leibovitz medium (Gibco, pH 7.3±0.1) supplemented with bovine serum albumin (3 mg.ml$^{-1}$), L-glutamine (0.23 mM), sodium pyruvate (2 mM) and hypoxanthine (4 mM) is used as preparation medium. The antral follicles of the ovaries are punctured under a dissecting microscope using two 27-gauge needles attached to two 1 ml syringes. Cumulus enclosed oocytes (CEO) of uniform size are selected with a mouth-controlled pipette and rinsed in 0,5 ml fresh preparation medium. About 20 CEO are obtained from one ovary.

Isolation of Denuded Oocytes:

Oocytes freed from cumulus cells, i.e. denuded oocytes (DO), are obtained by gently flushing CEO through a fine-bore mouth-controlled pipette. DO were collected in fresh MEM alpha medium, containing bovine serum albumin (3 mg.ml$^{-1}$), L-glutamine (0.23 mM), sodium pyruvate (2 mM) and hypoxanthine (4 mM), and washed twice before transfer to the test medium.

Experimental Design:

The oocyte assay is performed in 3 blocks, each block represents the ovaries of one mouse (randomized block design). At t=0 DO or CEO of the first ovary of the first mouse, are spread over well 1 and 3 and oocytes of the second ovary over well 2 and 4 of a 4-well multidish containing 0.5 ml of culture medium to which a 22S-hydroxycholesta-8,14-diene derivative of the invention is added [first block]. Culture medium was used as control. The same procedure is performed for the second and third mouse [block 2 and 3]. The culture medium used is MEM alpha medium (Gibco, pH 7.3±0.1) saturated with $CO_2$ and supplemented with bovine serum albumin (3 mg.ml$^{-1}$), L-glutamine (0.23 mM), sodium pyruvate (2 mM) and hypoxanthine (4 mM). In total, each control or test compound is tested on 30 oocytes (10 oocytes per block). At t=0 the number of oocytes with intact germinal vesicles (GV) or germinal vesicle break-down (GVBD) is counted under an inverted microscope with differential interference contrast equipment. Only oocytes with an intact GV are used in the experiment. Oocytes are cultured 22 hours at 37° C. in 100% humidified atmosphere with 5% $CO_2$ in air. At the end of the culture period the number of oocytes with GV or GVBD per group is counted. For statistical analysis the percentage germinal vesicle breakdown is calculated for each group in one block. These percentages are subjected to arcsin transformation, and differences between control and test compounds are analyzed by an ANOVA test for a randomized block design. Results are presented in Table I.

TABLE I

Percentage germinal vesicle breakdown (GVBD) in oocytes following culturing in the presence of test compounds in agonistic testing.

| Compound[1] | % GVBD DO assay exp. (control) | CEO assay exp. (control) |
|---|---|---|
| (3β,5α,20S,22S)4,4-dimethylcholesta-8,14-diene-3,22-diol (Example 1) | 85(0) | 6(3) |
| (3β,5α,20S,22S)-4,4-dimethylcholesta-8,14,24-triene-3,22-diol (Example 2) | 97(2) | 73(2) |
| (3β,5α,20R)4,4-dimethylcholesta-8,14,24-trien-3-ol (FF-Mas)[2] | 84(7) | 0(0) |

[1]Each compound was tested at a concentration of 5 μM.
[2]Tested at a concentration of 10 μM.

What is claimed is:

1. A meiosis activating compound having the general formula I:

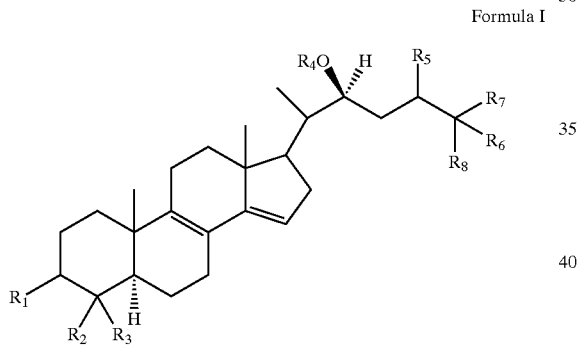

Formula I wherein
 $R_1$ is OR, $OSO_3H$ or =NOR; with R being H, $(C_{1-6})$alkyl or $(C_{1-6})$acyl;
 each $R_2$ and $R_3$ is independently hydrogen or $(C_{1-6})$alkyl;
 $R_4$ is hydrogen, $(C_{1-6})$alkyl or $(C_{1-6})$acyl;
 $R_5$ is hydrogen; or $R_5$ designates, together with $R_6$, an additional bond between carbon atoms at which $R_5$ and $R_6$ are placed;
 $R_6$ is hydrogen, hydroxy or halogen; or $R_6$ designates, together with $R_5$, an additional bond between carbon atoms at which $R_6$ and $R_5$ are placed;
 each $R_7$ and $R_8$ is independently hydrogen or $(C_{1-4})$alkyl;
or a pharmaceutically acceptable salt thereof.

2. The meiosis activating compound according to claim 1, wherein C-20 has the 20S configuration.

3. The meiosis activating compound of claim 2, wherein $R_1$ is OR, wherein R is H or $(C_{1-6})$acyl, and the configuration of the 3-OR substituent is the β-configuration.

4. A 22S-hydroxycholesta-8,14-diene derivative selected from the group consisting of (3β,5α,20S,22S)-4,4-dimethylcholesta-8,14-diene-3,22-diol and (3β,5α,20S, 22S)-4,4-dimethylcholesta-8,14,24-triene-3,22-diol.

5. A method for meiosis activation, comprising:
 administering an effective amount of the meiosis activating compound according to claim 1.

6. A pharmaceutical composition, comprising:
 a meiosis activating compound according to claim 1 in admixture with at least one pharmaceutically acceptable auxiliary.

7. The meiosis activating compound of claim 1, wherein each of $R_7$ and $R_8$ is independently $(C_{1-4})$alkyl substituted with OH, $(C_{1-4})$alkoxy, or halogen.

8. The meiosis activating compound according to claim 1, wherein R is selected from the group consisting of hydrogen, a hexyl group, a pentyl group, a butyl group, an isobutyl group, a tertiary butyl group, a propyl group, an isobutyl group, a tertiary butyl group, a propyl group, an isopropyl group, an ethyl group, a methyl group, a hexanoyl group, a pentaoyl group, a pivaloyl group, a butyrl group, a propanoyl group, an acetyl group, a formyl group, a hemiglutaroyl group, hemi succinoyl group, and a hemi-maloyl group.

9. The meiosis activating compound according claim 1, wherein each of $R_2$ and $R_3$ is selected from the group consisting of hydrogen, a hexyl group, a pentyl group, a butyl group, an isobutyl group, a tertiary butyl group, a propyl group, an isopropyl group, an ethyl group, and a methyl group.

10. The meiosis activating compound according to claim 1, wherein $R_4$ is selected from the group consisting of hydrogen, a hexyl group, a pentyl group, a butyl group, an isobutyl group, a tertiary butyl group, a propyl group, an isopropyl group, an ethyl group, a methyl group, a hexanoyl group, a pentaoyl group, a pivaloyl group, a butyrl group, a propanoyl group, an acetyl group, a formyl group, a hemiglutaroyl group, hemi succinoyl group, and a hemi-maloyl group.

11. The meiosis activating compound according to claim 7, wherein each of $R_7$ and $R_8$ is independently selected from the group consisting of hydrogen, a butyl group, an isobutyl group, a tertiary butyl group, a propyl group, an isopropyl group, an ethyl group, and a methyl group.

* * * * *